(12) United States Patent
Sanjeevappa et al.

(10) Patent No.: US 12,402,820 B2
(45) Date of Patent: Sep. 2, 2025

(54) SUCTION MANIFOLD ASSEMBLY FOR AN ELECTROCARDIOGRAM ELECTRODE APPLICATION SYSTEM

(71) Applicant: GE Precision Healthcare LLC, Wauwatosa, WI (US)

(72) Inventors: Manjunatha Kaankanhalli Sanjeevappa, Bangalore (IN); Gangadhar Ippili, Bangalore (IN); Robin Mathew Issac, Bangalore (IN); Sirosh Sivasankaran, Bangalore (IN); Oswin Varghese, Bangalore (IN); Sharla Rae Filtz, Cedarburg, WI (US); Caitlin Theresa Strobel, New Castle, PA (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 706 days.

(21) Appl. No.: 17/733,361

(22) Filed: Apr. 29, 2022

(65) Prior Publication Data

US 2023/0346282 A1    Nov. 2, 2023

(51) Int. Cl.
*A61B 5/252*    (2021.01)
*A61B 5/282*    (2021.01)

(52) U.S. Cl.
CPC .............. *A61B 5/252* (2021.01); *A61B 5/282* (2021.01)

(58) Field of Classification Search
CPC .......... A61B 5/252; A61B 5/282; A61B 5/303
See application file for complete search history.

(56) References Cited

U.S. PATENT DOCUMENTS

| 3,307,817 A | 3/1967 | Cocito |
| 2003/0195408 A1 | 10/2003 | Hastings et al. |

(Continued)

FOREIGN PATENT DOCUMENTS

| DE | 19541627 A1 * | 5/1997 | ......... A61B 5/04082 |
| EP | 0776629 A2 | 6/1997 | |
| WO | WO-2013013962 A1 * | 1/2013 | ............. A61B 5/252 |

OTHER PUBLICATIONS

Zelinski, P., "Additive Manufacturing's Manifold Benefits", https://www.additivemanufacturing.media/articles/additive-manufacturings-manifold-benefits (Year: 2012).*

*Primary Examiner* — Linda C Dvorak
*Assistant Examiner* — William Mossbrook
(74) *Attorney, Agent, or Firm* — Fletcher Yoder, P.C.

(57) ABSTRACT

An ECG electrode application system includes an electrode distributor including a housing and a suction manifold assembly disposed within the housing. The suction manifold assembly includes a manifold, a plurality of pneumatic valves integrated within the manifold, and the manifold includes a common manifold chamber fluidly coupled to each pneumatic valve, and each pneumatic valve includes a venturi passage. The ECG electrode application system includes a plurality of suction electrodes, each suction electrode having an electrode suction dome and coupled to the electrode distributor via a lead wire, and each lead wire is coupled to a respective pneumatic valve. Each electrode suction dome is configured when pressed to cause a change in air pressure that results in a suction pressure being applied within a respective electrode suction dome to adhere a corresponding suction electrode to a subject at a pressure determined by the venturi passage of a corresponding pneumatic valve.

18 Claims, 10 Drawing Sheets

(56) References Cited

U.S. PATENT DOCUMENTS

| | | | |
|---|---|---|---|
| 2006/0161068 A1* | 7/2006 | Hastings | A61B 5/28 600/509 |
| 2013/0058805 A1* | 3/2013 | Chien | F04B 43/1133 417/395 |
| 2014/0336599 A1 | 11/2014 | Patel et al. | |

* cited by examiner

SUCTION MANIFOLD ASSEMBLY FOR AN ELECTROCARDIOGRAM ELECTRODE APPLICATION SYSTEM

BACKGROUND

The subject matter disclosed herein relates to an electrocardiogram (ECG) electrode application system.

A variety of physiological parameters may be measured by monitoring electrical signals within the body. Monitoring systems utilizing electrodes may be utilized to monitor the transfer of electrical energy within the body of a patient. For example, a monitoring system may include an ECG monitoring system that utilizes electrodes (e.g., ECG electrodes) to monitor heart activity during various states (e.g., resting and/or exercise). Some ECG monitoring systems may utilize electrodes (e.g., suction electrodes) that are adhered to the patient's skin via negative pressure (e.g., due to a vacuum). In certain aspects, these suction electrodes may be adhered via negative pressure to the patient in response to a trigger (e.g., pressing a dome associated with the suction electrode). However, the sensitivity of the trigger (e.g., electrode dome) may require a large amount of force to trigger the negative pressure. Sometimes an electrode dome may need to be pressed multiple times to trigger the negative pressure. In addition, the negative pressure (e.g., suction pressure) may be too little resulting in failure to acquire an ECG signal via the electrode due to insufficient contact of the electrode with the patient. Also, the negative pressure may be too much resulting in a wound or cut on the skin of the patient.

BRIEF DESCRIPTION

Certain aspects commensurate in scope with the originally claimed subject matter are summarized below. These aspects are not intended to limit the scope of the claimed subject matter, but rather these aspects are intended only to provide a brief summary of possible aspects. Indeed, the subject matter may encompass a variety of forms that may be similar to or different from the aspects set forth below.

In one aspect, an electrocardiogram (ECG) electrode application system is provided. The ECG electrode application system includes an electrode distributor. The electrode distributor includes a housing and a suction manifold assembly disposed within the housing. The suction manifold assembly includes a manifold, a plurality of pneumatic valves integrated within the manifold, and the manifold includes a common manifold chamber fluidly coupled to each pneumatic valve of the plurality of pneumatic valves, and each pneumatic valve includes a venturi passage. The ECG electrode application system also includes a plurality of suction electrodes, each suction electrode of the plurality of suction electrodes having an electrode suction dome and coupled to the electrode distributor via a lead wire, and each lead wire is coupled to a respective pneumatic valve. Each electrode suction dome is configured when pressed to cause a change in air pressure that results in a suction pressure being applied within a respective electrode suction dome to adhere a corresponding suction electrode to a subject at a pressure determined by the venturi passage of a corresponding pneumatic valve.

In another aspect, a suction manifold assembly for an ECG electrode application system is provided. The suction manifold assembly includes a manifold. The suction manifold assembly also includes a plurality of pneumatic valves integrated within the manifold. The suction manifold assembly also includes a common manifold chamber fluidly coupled to each pneumatic valve of the plurality of pneumatic valves, and wherein each pneumatic valve is configured to be coupled via a lead wire to a respective suction electrode. The suction manifold assembly is configured to be disposed within a housing of an electrode distributor of the ECG application system. The pneumatic valves of the plurality of pneumatic valves are disposed adjacent to each other along a horizontal plane in both a first direction and a second direction, the first direction being orthogonal to the second direction.

In a further aspect, an ECG electrode application system is provided. The ECG electrode application system includes an electrode distributor. The electrode distributor includes a housing and a suction manifold assembly disposed within the housing. The suction manifold assembly includes a manifold, a plurality of pneumatic valves integrated within the manifold, and the manifold includes a common manifold chamber fluidly coupled to each pneumatic valve of the plurality of pneumatic valves. The ECG electrode system also includes an orifice disposed within the common manifold chamber. The ECG electrode application system further includes a plurality of suction electrodes, each suction electrode of the plurality of suction electrodes having an electrode suction dome and coupled to the electrode distributor via a lead wire, and each lead wire is coupled to a respective pneumatic valve. Each electrode suction dome is configured when pressed to cause a change in air pressure that results in a suction pressure being applied within a respective electrode suction dome to adhere a corresponding suction electrode to a subject at a pressure determined by the venturi passage of a corresponding pneumatic valve, and the orifice is configured to set a level of change in the air pressure to trigger the application of the suction pressure applied within a respective electrode suction dome.

BRIEF DESCRIPTION OF THE DRAWINGS

These and other features, aspects, and advantages of the present subject matter will become better understood when the following detailed description is read with reference to the accompanying drawings in which like characters represent like parts throughout the drawings, wherein.

DETAILED DESCRIPTION

Figure 1:
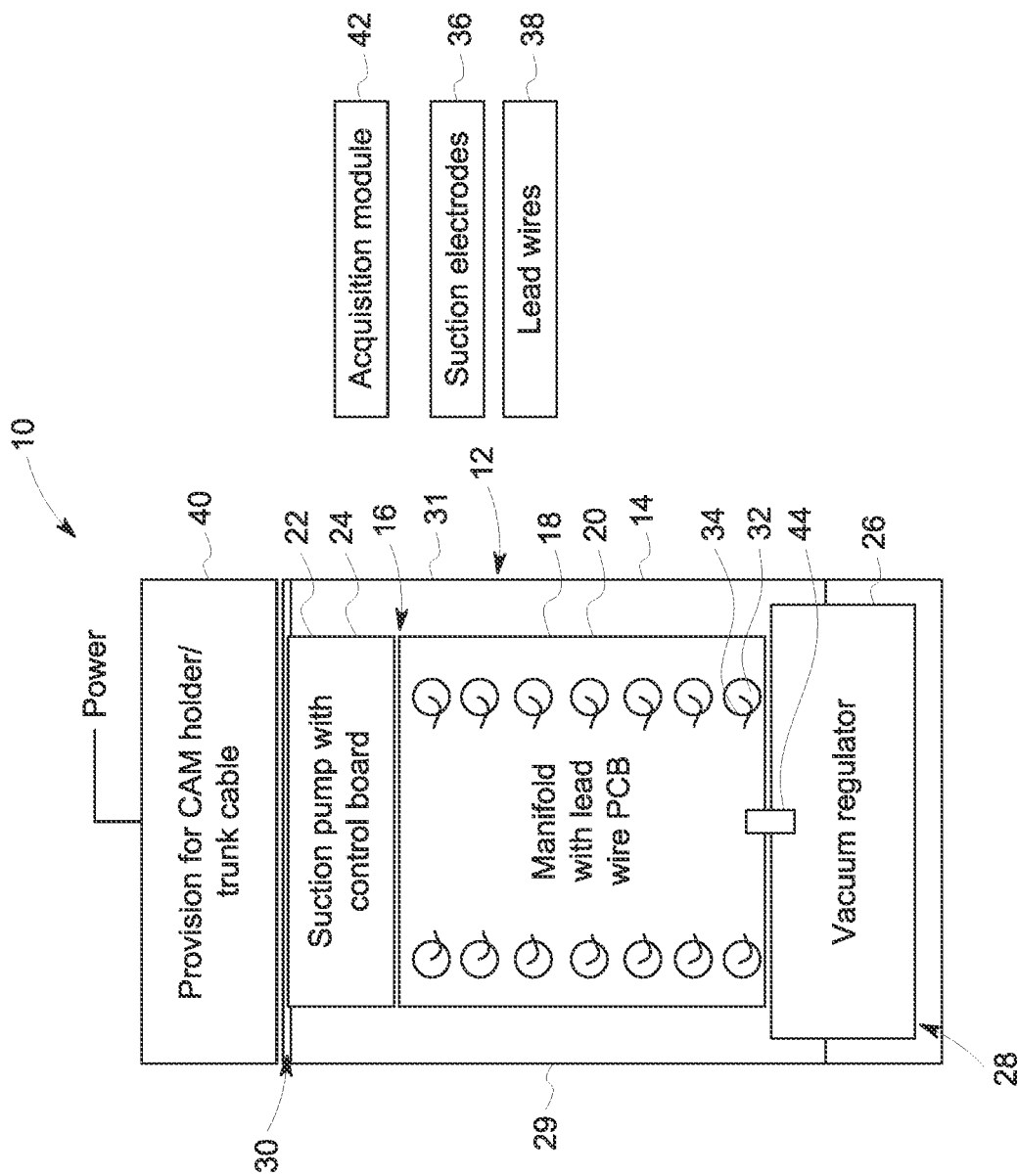
FIG. 1 is a schematic diagram of an ECG electrode application system, in accordance with aspects of the present disclosure.

One or more specific aspects will be described below. In an effort to provide a concise description of these aspects, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various aspects of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed aspects.

The present disclosure provides for an ECG electrode application system to monitor ECG activity of a patient in various states (e.g., during and exercise). In particular, the ECG electrode application system may include an electrode distributor that includes a housing that includes a suction manifold assembly disposed within. Leads of suction electrodes (e.g., suction ECG electrodes) may be coupled to a bottom surface of the electrode distributor. In certain aspects, these leads may extend in a vertical direction from the bottom surface of the electrode distribution system to eliminate or minimize bending stresses in the leads, thus, improving the life spans of the leads. The suction manifold assembly includes a manifold. The manifold includes a plurality of pneumatic valves integrated within the manifold. Adjacent pneumatic valves may be arranged in both a first direction and a second direction (which are orthogonal with respect to each other) along a horizontal plane. Each pneumatic valve is fluidly coupled to a common manifold chamber of the manifold. Each lead wire is fluidly coupled to a corresponding pneumatic valve. Each pneumatic valve includes a venturi path integrated within the manifold. The venturi path determines the negative pressure (e.g., suction dome pressure) with which the suction electrode is adhered to the skin of a patient. An orifice is disposed with the common manifold chamber. The orifice determines the sensitivity (e.g., by controlling mass flow rate within the system) for pressing the suction dome to trigger a pump (e.g., disposed within the electrode distributor) to cause a vacuum to create the negative pressure for adhering the suction electrodes to the skin of the patient. The utilization of the venturi paths enables a compact manifold. The combination of the venturi paths and the orifice improves triggering the use of a pump and provides sufficient vacuum transfer pressure to the suction electrodes.

FIG. 1 is a schematic diagram of an ECG electrode application system 10 according to an example. The ECG electrode application system 10 enables ECG activity to be acquired and monitored for a patient in various states (e.g., during and exercise). The ECG electrode application system 10 includes an electrode distributor 12 having a housing 14. The electrode distributor 12 includes a suction manifold assembly 16 disposed within the housing 14. The suction manifold assembly 16 includes a manifold 18 coupled to a lead wire printed circuit board (PCB) 20. The electrode distributor 12 also includes a pump 22 (e.g., suction or vacuum pump) and a control board 24 (e.g., pressure sensor board) for the pump 22 disposed within the housing 14. The pump 22 is coupled to the manifold 18 via tubing. A regulator 26 (e.g., vacuum regulator) is coupled to an end 28 of the manifold 18 opposite an end 30 where the pump 22 is located.

The suction manifold assembly 16 includes a plurality of pneumatic valves 32 (e.g., suction lead valves) integrated within the manifold 18. The number of pneumatic valves 32 integrated within the manifold 18 may vary. As depicted, the number of pneumatic valves 32 is 14. In certain aspects, the number of pneumatic valves 32 may be 10, 12, or another number. As described in greater detail below, adjacent pneumatic valves 32 may be arranged in a first direction and a second direction (that are orthogonal with respect to each other) along a horizontal plane (e.g., extending form end 28 to end 30 and from side 29 to side 31). Each pneumatic valve 32 includes a venturi path or passage 34. A portion of each pneumatic valve 32 (including the venturi path 34) may be additively manufactured as part of the manifold 18. The manifold 18 includes a common manifold chamber which is fluidly coupled to each pneumatic valve 32. The venturi paths 34 enable the manifold 18 to be more compact compared to other manifolds associated with other ECG electrode application systems.

The ECG electrode application system 10 includes suction electrodes 36 (e.g., ECG electrodes) that are coupled to the lead wires 38. Each lead wire 38 of the suction electrodes 38 is configured to couple (e.g., via a port connector) to a surface (e.g., bottom surface) of the electrode distributor 12 via ports. Each lead wire 38 includes pneumatic tubing and may be made of a conductive plastic. When coupled to the ports, the lead wires are coupled to and provide to the lead wire PCB 20 electrical signals (ECG signals) from the suction electrodes 36. When coupled to the ports, the pneumatic tubing of each lead wire 38 is fluidly coupled to a respective manifold port associated with a respective pneumatic valve 32.

The ECG electrode application system 10 includes an area or provision 40 for holding and coupling an acquisition module 42 to the electrode distributor 12 (e.g., electrode block distributor). The electrode distributor 12 includes a PCB board that couples to the acquisition module 42 when the acquisition module is coupled to the electrode distributor 12. Electrical signals from the electrode sensors are passed from the lead wire PCB 20 to the PCB board coupled to the acquisition module 42 and then to the acquisition module 42. The acquisition module 42 acquires the analog ECG signals from the suction electrodes 36, digitizes them, and sends them to a host system. The area or provision 40 also enables a trunk cable (e.g., having a pneumatic tubing connector) to be coupled to the lead wires 38 via the suction manifold assembly 16. The ECG electrode application system 10 receives power from a power supply (not shown).

The lead wires 38, the suction manifold assembly 16, the regulator 26, and the control board 24, and the pump 22 form a system that enables air to flow at a certain mass flow rate (e.g., $3.04 \times 10^5$ kg/s) and air velocity. The vacuum regulator 26 is coupled to an orifice 44 that extends into manifold 18. An inner diameter of the orifice 44 determines a level of change in air pressure (i.e., the sensitivity of the electrode dome of each suction electrode 36) that will trigger the pump 22 to create a vacuum or suction pressure in the system. The orifice 44 minimizes the number of presses of the suction dome of a respective suction electrode 36. The regulator 26 is configured to alter the amount of vacuum or suction pressured applied (e.g., between approximately 150 to 195 mmHg).

Each suction electrode 36 includes an electrode (e.g., silver/silver chloride electrode) and a suction dome (e.g., made of a conductive plastic) disposed about the electrode. Each suction electrode 36 may also include a filter disk. To apply the suction electrode 36 to the skin of a patient, the suction dome is pressed and released (e.g., via a finger) which generates a small air pressure or change in air pressure (e.g., approximately 5 to 10 mmHg) in the system. In particular, pressing the suction dome compresses and pressurizes the air in the system. The air pressure actuates the pneumatic valve 32 associated with the suction electrode 36 and opens the venturi passage 34 to the air path. The small, pressurized air passes through the lead wires 38, the manifold 18 (including the pneumatic valve 32), and the regulator 26 to the pressure sensor on the control board 24. The control board 24 senses the change in air pressure and triggers the pump 22 for actuation. Upon the vacuum being applied in the system, the suction electrode 36 adheres and holds its place on the skin of the patient. The suction dome pressure of the suction electrode 36 adhering to the patient is determined by the venturi path 34. The venturi path 34 provides the proper required pressure to adhere the suction electrode 36 to acquire an ECG signal without wounding or cutting the skin of the patient. The venturi path 34 also increases the mass flow of air in the system, which is controlled by the orifice 44.

Figure 2:
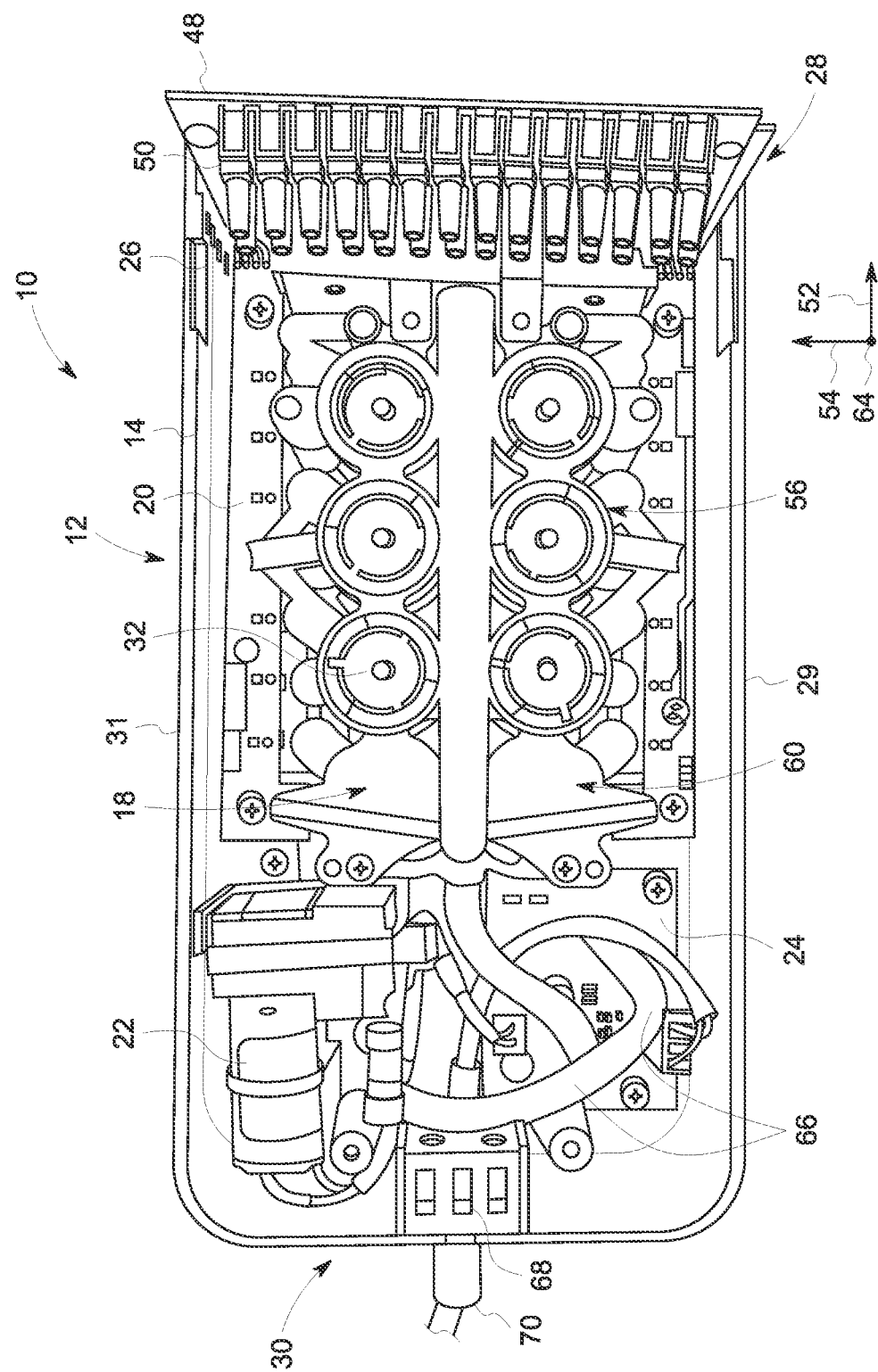
FIG. 2 is a top view of an electrode distributor coupled to a regulator of the ECG electrode application system in FIG. 1, in accordance with aspects of the present disclosure.

FIG. 2 is a top view of an electrode distributor 12 coupled to the regulator 26 of the ECG electrode application system 10 in FIG. 1, according to an example. The electrode distributor 12 includes a wall 46 defining the housing 14. The wall 46 defines a bottom surface (not shown, see FIG. 13), the end 30, and the sides 29 and 31. The regulator 26 is coupled to end 28 of the electrode distributor 12 to close it off. A lid (not shown, see FIG. 12) couples to the electrode distributor 12 to enclose the internal components (e.g., the pump 22, the suction manifold assembly 16, etc.) within the electrode distributor 12. As depicted in FIG. 2, a PCB board 48 includes connections 50 for coupling to an acquisition module (e.g., acquisition module 42 in FIG. 1).

Figure 3:
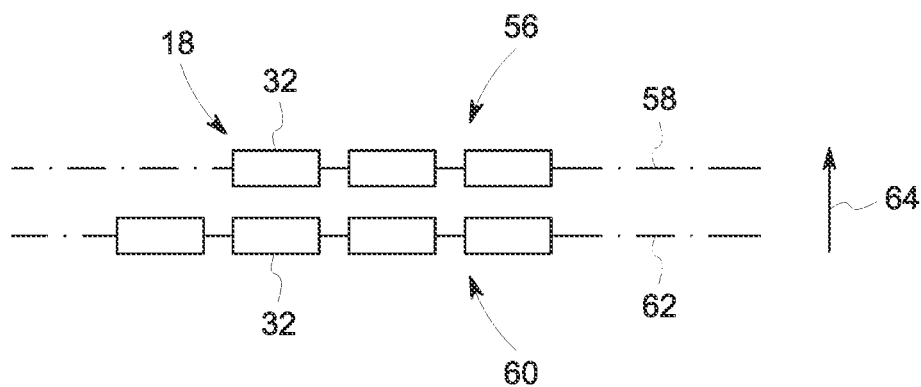
FIG. 3 is a side schematic view of pneumatic valves of a manifold of the electrode application system in FIG. 1 relative to horizontal planes, in accordance with aspects of the present disclosure.

As depicted in FIG. 2, the manifold 18 is disposed on and coupled to the lead wire printed circuit board (PCB) 20. The lead wire PCB 20 is electrically coupled to the lead wires of the suction electrodes. The plurality of pneumatic valves 32 are integrated within the manifold 18. As depicted, the pneumatic valves 32 are disposed adjacent to each other along a horizontal plane in a first direction 52 (e.g., extending from end 28 to end 30) and second direction 54 extending from side 29 to side 31. The first direction 52 is orthogonal to the second direction 54. In particular, a first set 56 of the pneumatic valves 32 extend in both the first direction 52 and the second direction 54 along a horizontal plane 58 (see FIG. 3). A second set 60 of the pneumatic valves 32 extend in both the first direction 52 and the second direction 54 along another horizontal plane 62 (see FIG. 3) that is different from and parallel with the horizontal plane 58. The first set 56 of the pneumatic valves 32 is located above the second set 60 of pneumatic valves 32 in direction 64 (which is orthogonal with respect both the first direction 52 and the second direction 54). In particular, first set 56 of the pneumatic valves 32 is disposed more adjacent to the top surface (i.e., the lid) of the housing 14 of the electrode distributor 12, while the second set 60 of pneumatic valves 32 is disposed more adjacent to the bottom surface of the housing 14. Some of the pneumatic valves 32 in the first set 56 are vertically aligned with (along the direction 64) with some of the pneumatic valves 32 in the second set 60. The first set 56 of the pneumatic valves 32 and the second set of pneumatic valves 32 are oriented in opposite directions as depicted in FIG. 2. In particular, a retainer ring (see FIGS. 13 and 14) of each pneumatic valve 32 of the first set 56 faces the top surface (i.e., the lid) of the housing 14, while the retainer ring of each pneumatic valve 32 of the second set 60 faces the bottom surface of the housing 14. As depicted, the first set 56 of pneumatic valves 32 includes 6 pneumatic valves 32 and the second set 60 of pneumatic valves 32 includes 8 pneumatic valves 32.

As depicted in FIG. 2, tubing 66 connects the pump 22 to the manifold 18. In addition, the tubing 66 connects manifold 18 to the control board 24 having the pressure sensor. The control board 24 is also connected to the pump 22. The electrode distributor 12 also includes a connection 68 for coupling to a trunk cable 70 (e.g., having a pneumatic tubing connector).

Figure 4:
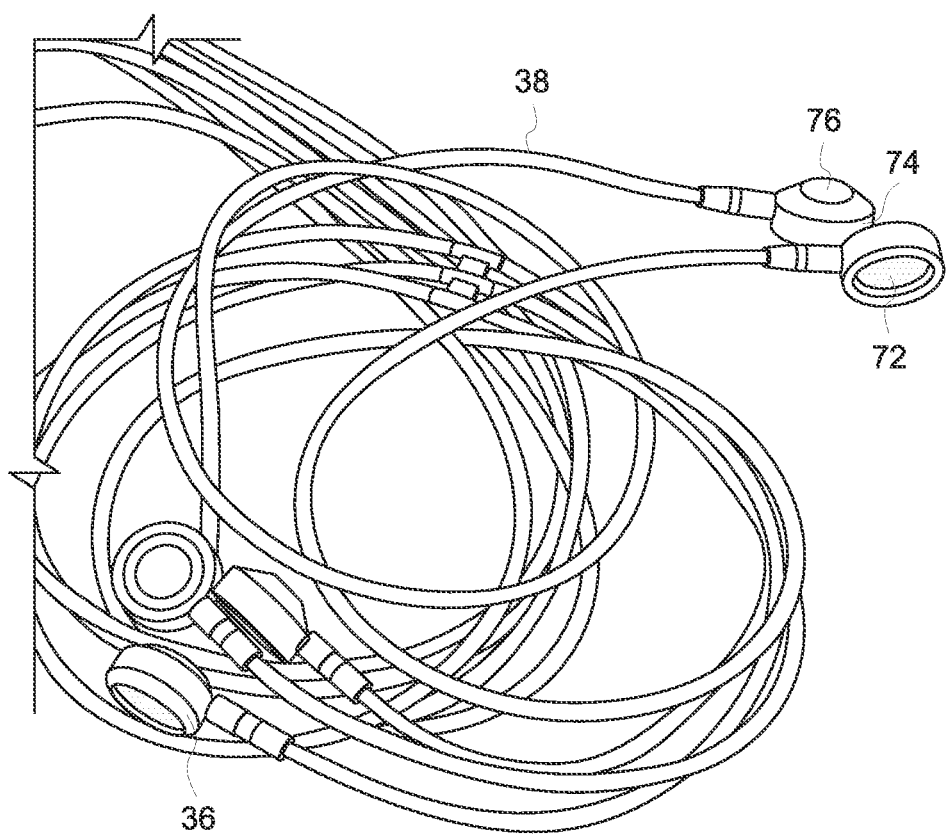
FIG. 4 is a perspective view of a plurality of suction electrodes of the electrode application system in FIG. 1 coupled to respective leads, in accordance with aspects of the present disclosure.
Figure 5:
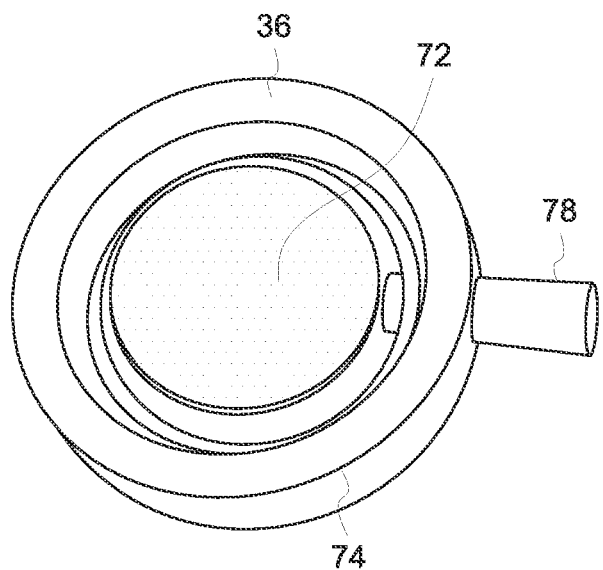
FIG. 5 is a perspective view of a bottom surface (e.g., patient interfacing surface) of a suction electrode of FIG. 4, in accordance with aspects of the present disclosure.

FIGS. 4 and 5 illustrate different views of the suction electrodes 36 (e.g., ECG electrodes), according to an example. Each suction electrode 36 includes an electrode 72 (e.g., silver/silver chloride electrode) and a suction dome 74 (e.g., made of a conductive plastic) disposed about the electrode 72. Each suction electrode 36 may also include a filter disk. To apply the suction electrode 36 to the skin of a patient, a top portion 76 the suction dome 74 is pressed and released (e.g., via a finger) which generates a small air pressure or change in air pressure (e.g., negative air pressure) (e.g., approximately 5 to 10 mmHg) in the system. In particular, pressing the suction dome 74 compresses and pressurizes the air in the system. As depicted in FIG. 4, each suction electrode 36 is coupled to the lead wire 38 (e.g., having pneumatic tubing and made of conductive plastic). Each suction electrode 36 is coupled to the lead wire 38 via a connector 78.

Figure 6:
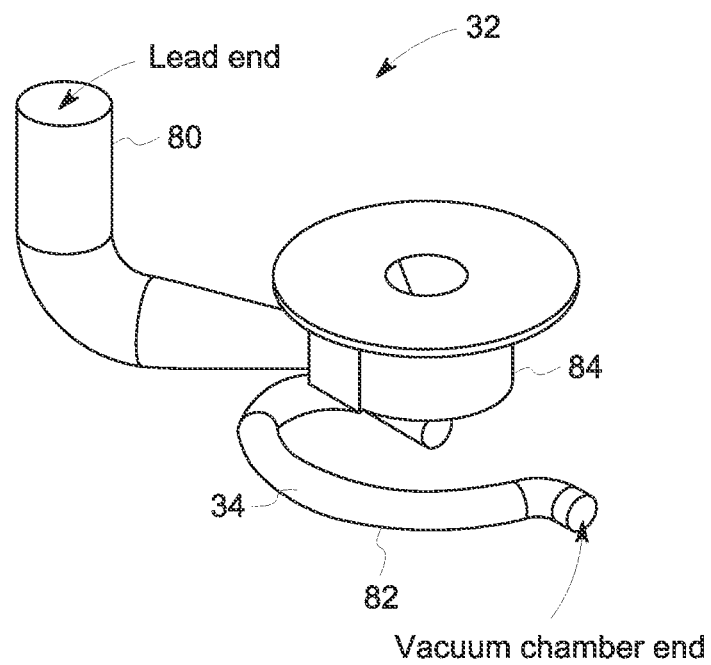
FIG. 6 is a perspective view of a portion of a pneumatic valve of the electrode system in FIG. 1 defined by a manifold, in accordance with aspects of the present disclosure.
Figure 7:
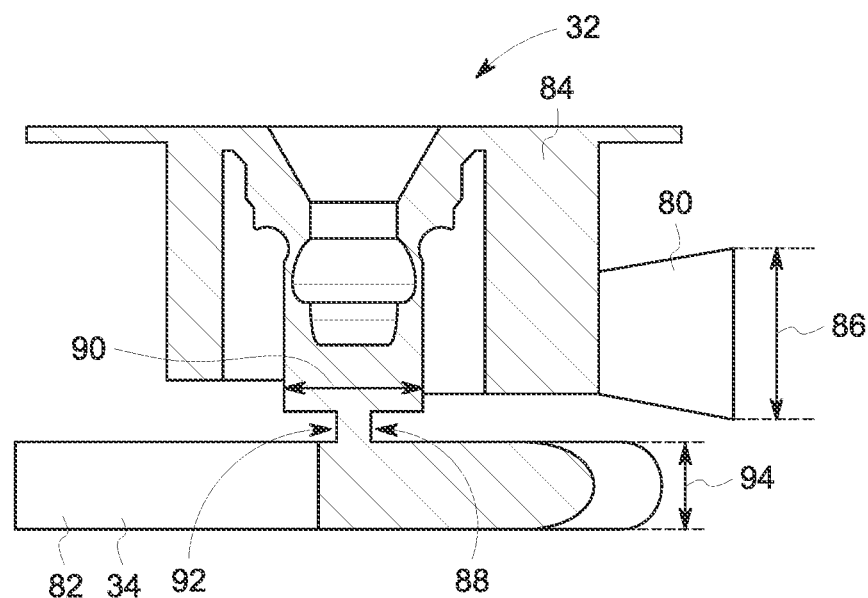
FIG. 7 is a cross-sectional view of the portion of the pneumatic valve in FIG. 6, in accordance with aspects of the present disclosure.

FIGS. 6 and 7 are different views of a portion of the pneumatic valve 32 defined by the walls of the manifold (e.g., manifold 18 in FIG. 1), according to an example. The pneumatic valve 32 includes an inlet portion 80 (e.g., manifold port portion) and an outlet portion 82 (e.g., forming the venturi path 34) coupled to a valve body portion 84 (e.g., central portion). The inlet portion 80, the outlet portion 82, and the valve body portion 84 are integral to the manifold. In particular, inlet portion 80, the outlet portion 82, and the valve body portion 84 may be additively manufactured (e.g., via stereolithography) as part of the manifold. After additive manufacturing, the additively manufactured portion of the pneumatic valve has pressurized air mixed with iso-propyl alcohol passed through (e.g., sometimes repeatedly) the manifold path to evacuate resins stuck in the air path to achieve the desired air pressure difference between the start and end of the air path.

The inlet portion 80 is fluidly coupled to the lead wire of a suction electrode. The outlet portion 82 is fluidly coupled to a common chamber (e.g., vacuum chamber) of the manifold. As described in greater detail below, the valve body portion 84 is configured to receive a plunger within, where the plunger changes positions relative to the valve body portion in response to pressure changes. A diameter 86 (see FIG. 7) of the inlet portion 80 narrows or tapers as it approaches the valve body portion 84. The valve body portion 80 includes a narrow portion 86 coupled to the outlet portion 82. The valve body portion 80 includes a diameter 90 adjacent the narrow portion 88. The narrow portion 86 includes a diameter 92. The outlet portion 82 includes a diameter 94 along its length. The diameter 92 is less than the diameter 90. The diameter 94 is less than the diameter 90 and greater than the diameter 92. The narrower diameter 92 in the narrow portion 88 creates a venturi effect in the flow of air from the valve body portion 80 to the outlet portion 82 (e.g., the venturi path 34). In certain aspects, the diameter 94 is approximately 2 millimeters (mm). In certain aspects, the diameter 92 is approximately 0.75 mm. In certain aspects, the diameter 92 may another value (e.g., approximately 0.64 mm or 1 mm). In certain aspects, the venturi path 34 may have a length of approximately 1.6 mm.

Figure 8:
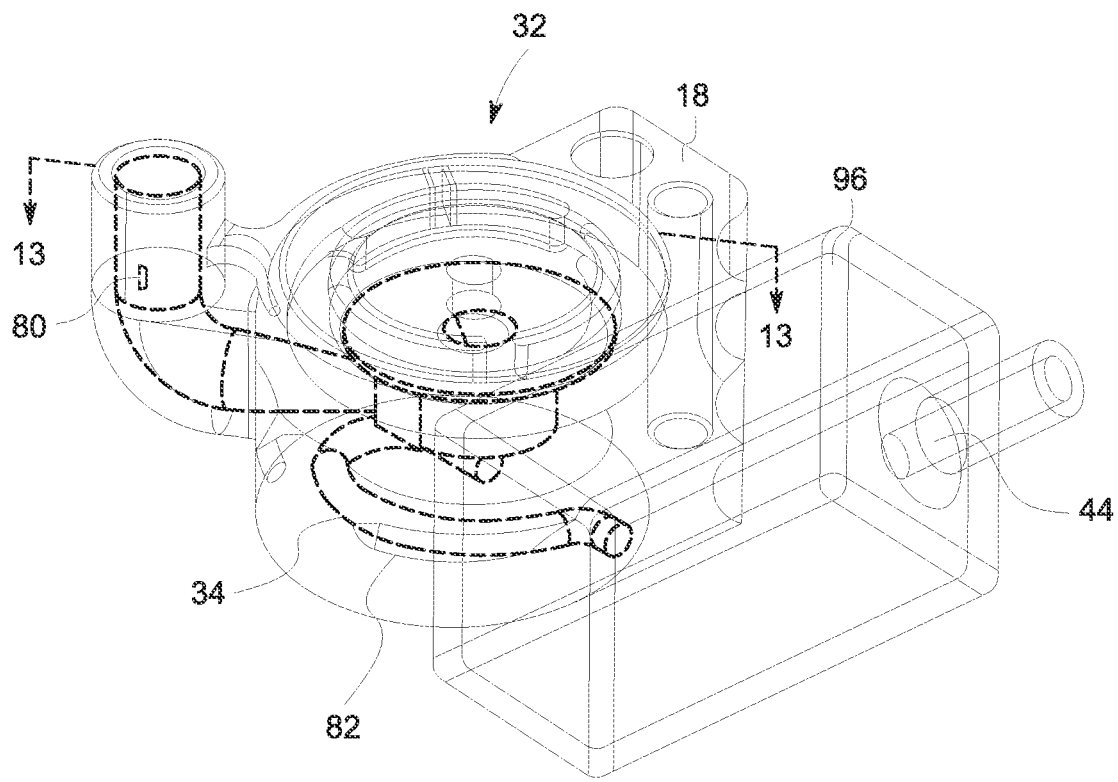
FIG. 8 is a perspective of a pneumatic valve of the electrode system in FIG. 1 coupled to a common manifold chamber, in accordance with aspects of the present disclosure.

FIG. 8 illustrates the inlet portion 80, the outlet portion 82, and the valve body portion 84 integrated within a portion of the manifold 18, according to an example. As depicted in FIG. 8, the outlet portion 82 or venturi path 34 extends into a common manifold chamber 96. As depicted in FIG. 8, the orifice 44 is extending into the common manifold chamber 96.

Figure 9:
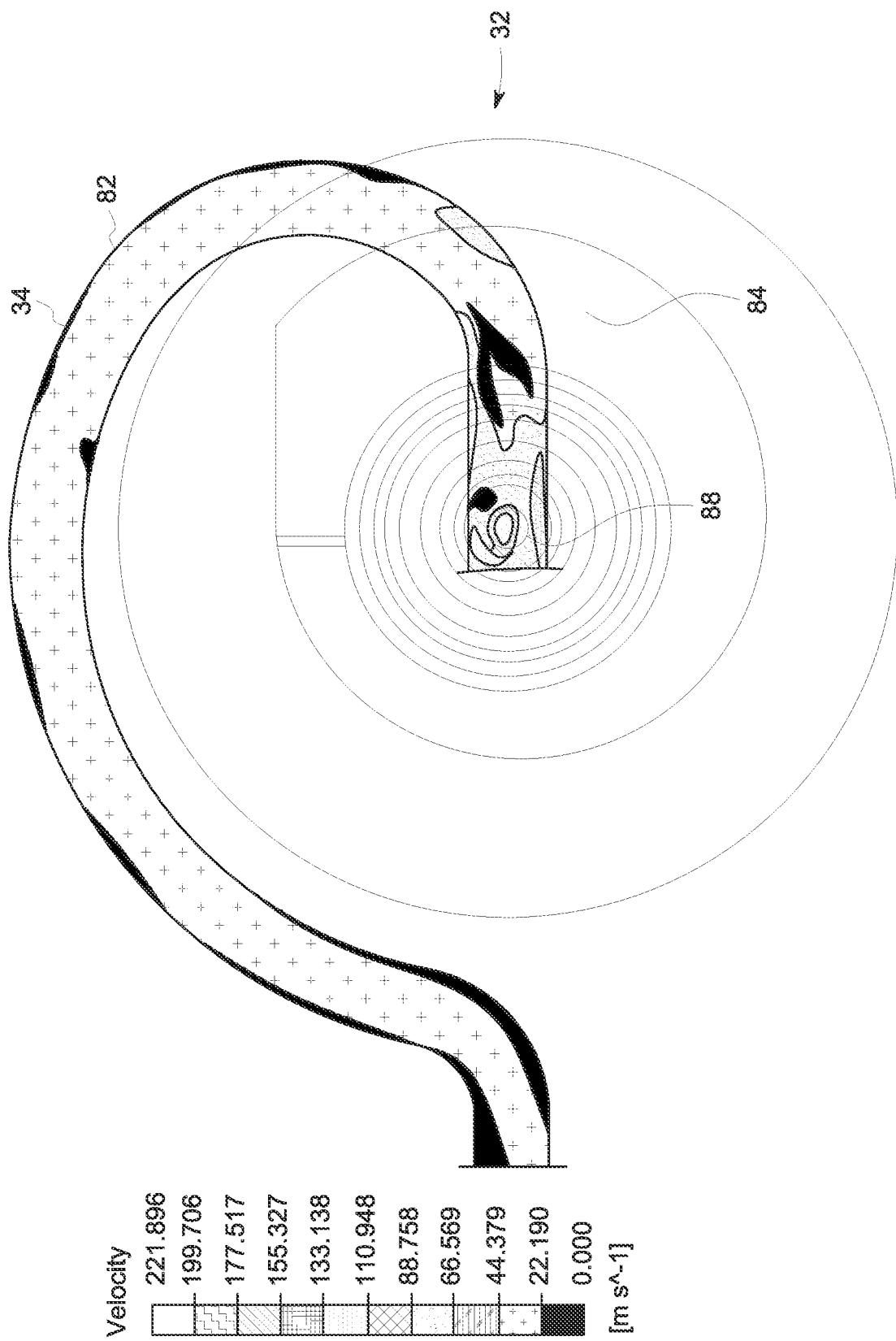
FIG. 9 illustrates the velocity of the air flow through a venturi path of the pneumatic valve in FIGS. 6-8 (e.g., via CFD modeling), in accordance with aspects of the present disclosure.

FIG. 9 illustrates the velocity of the air flow through the venturi path 34 of the pneumatic valve 32 in FIGS. 6-8 (e.g., where the narrow portion has a diameter of approximately 0.75 mm). The velocity of air flow is fairly low through the inlet portion (e.g. inlet portion 80 of FIG. 8) and the valve body portion 84 of the pneumatic valve 32. As depicted in FIG. 9, the velocity of the air flow significantly increases as it enters (e.g., via the narrow portion 88) the venturi path 34 or the outlet portion 82 from which it eventually exits. The velocity of the air flow is at its highest in narrow portion 88 as it enters the outlet portion 84 (e.g., due to the narrower diameter of the narrow portion 88). The velocity of the air flow is significantly higher in the outlet portion 84 than the inlet portion (e.g., inlet portion 80). The average inlet velocity of the air flow (e.g., into the inlet portion) is approximately 4.62 m/s. The average outlet velocity of the air flow (e.g., from the outlet portion 84) is approximately 30.313 m/s. The mass flow rate at outlet from the outlet portion 82 is approximately $8.09 \times 10^5$ kg/s.

Figure 10:
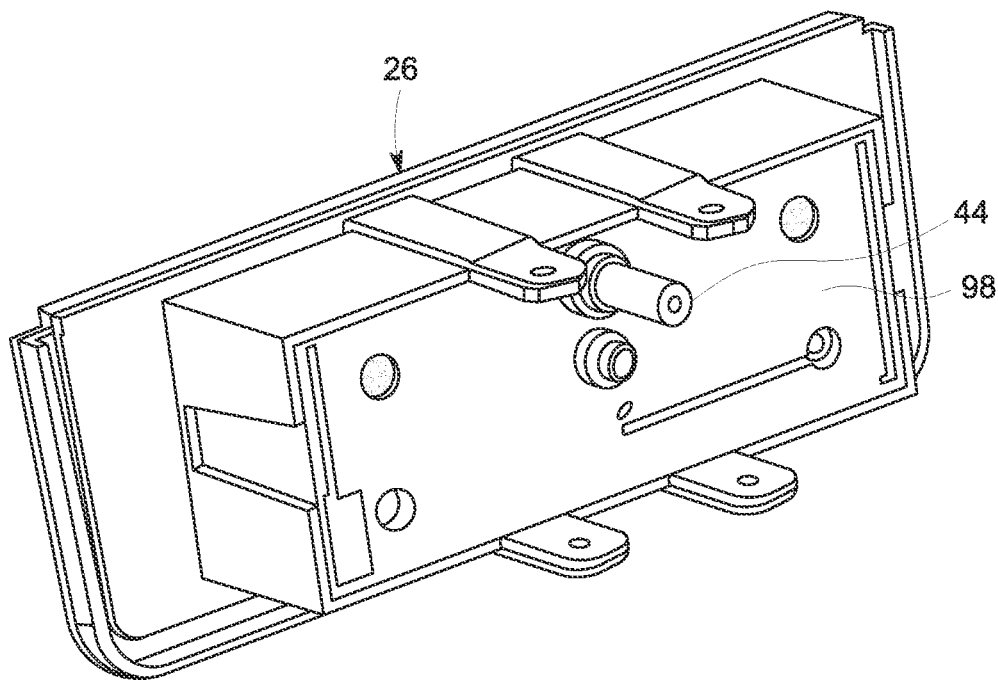
FIG. 10 is a perspective view of a regulator having an orifice of the ECG electrode application system in FIG. 1, in accordance with aspects of the present disclosure.
Figure 11:
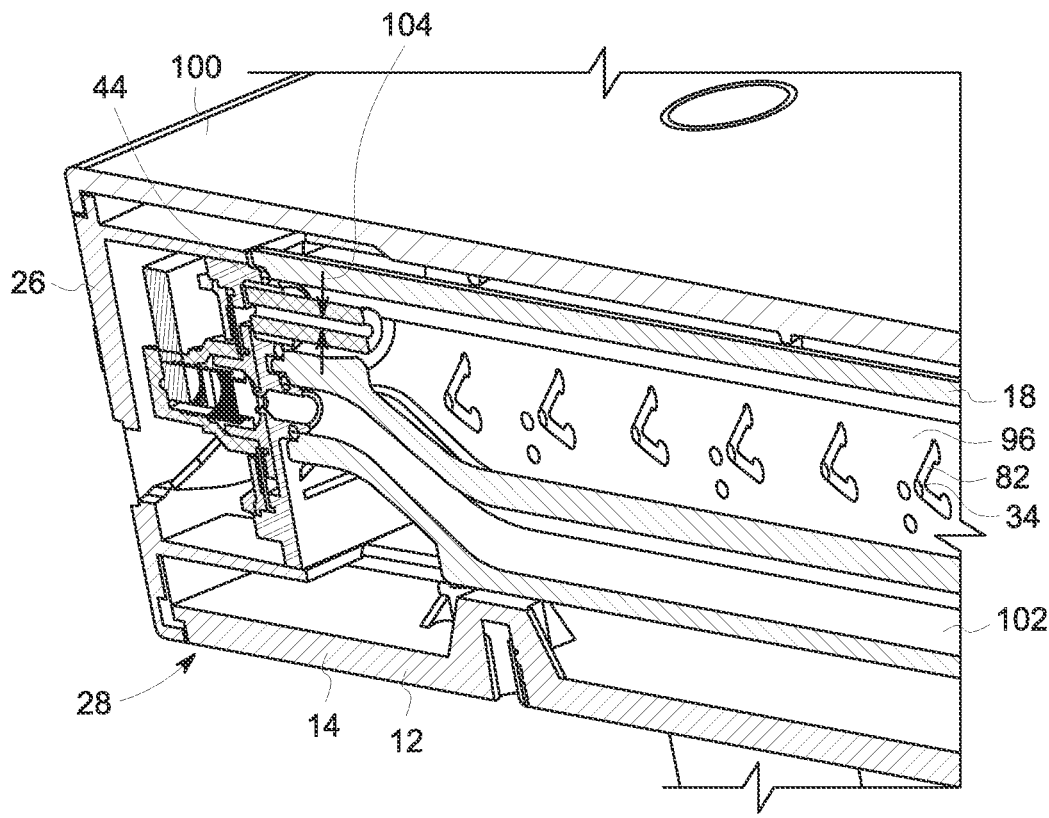
FIG. 11 is a cross-sectional view of the regulator having the orifice in FIG. 10 and a portion of an electrode distributor coupled to an electrode distributor, in accordance with aspects of the present disclosure.

FIG. 10 is a perspective view of the regulator 26 (e.g., vacuum regulator) having the orifice 44. The orifice 44 is coupled to an inner surface 98 (e.g., surface that faces an interior of an electrode distributor). The orifice 44 extends away from the surface 98 toward an interior of an electrode distributor. As depicted in FIG. 11, the regulator 26 is coupled the end 28 of the housing 14 of the electrode distributor 12. A lid 100 (e.g., forming a top surface) is disposed on the housing 14 and the regulator 26. The manifold 18 includes a lower chamber 102 and the common manifold chamber 96. The common manifold chamber 96 is fluidly coupled to the outlet portion 82 or venturi path 34 associated with each pneumatic valve. The lower chamber 102 and the common manifold chamber 96 are fluidly coupled to each other via the regulator 26. In particular, air flows between chamber 102 and the common manifold chamber 96 via the regulator 26. As depicted, the orifice 44 extends from the regulator 26 into the common manifold chamber 96. The orifice 44 includes an inner diameter 104. In certain aspects, the inner diameter 104 may be approximately 1.198 mm. The venturi air paths 34 increase the mass flow rate of air in the system and determine the suction pressure applied by each suction electrode. The inner diameter 104 of the orifice 44 controls the mass flow rate of the air in the system as well as the sensitivity of the pressing of the electrode dome of each suction electrode (i.e., the change in pressure needed to trigger the vacuum or suction pressure created by the pump).

Figure 12:
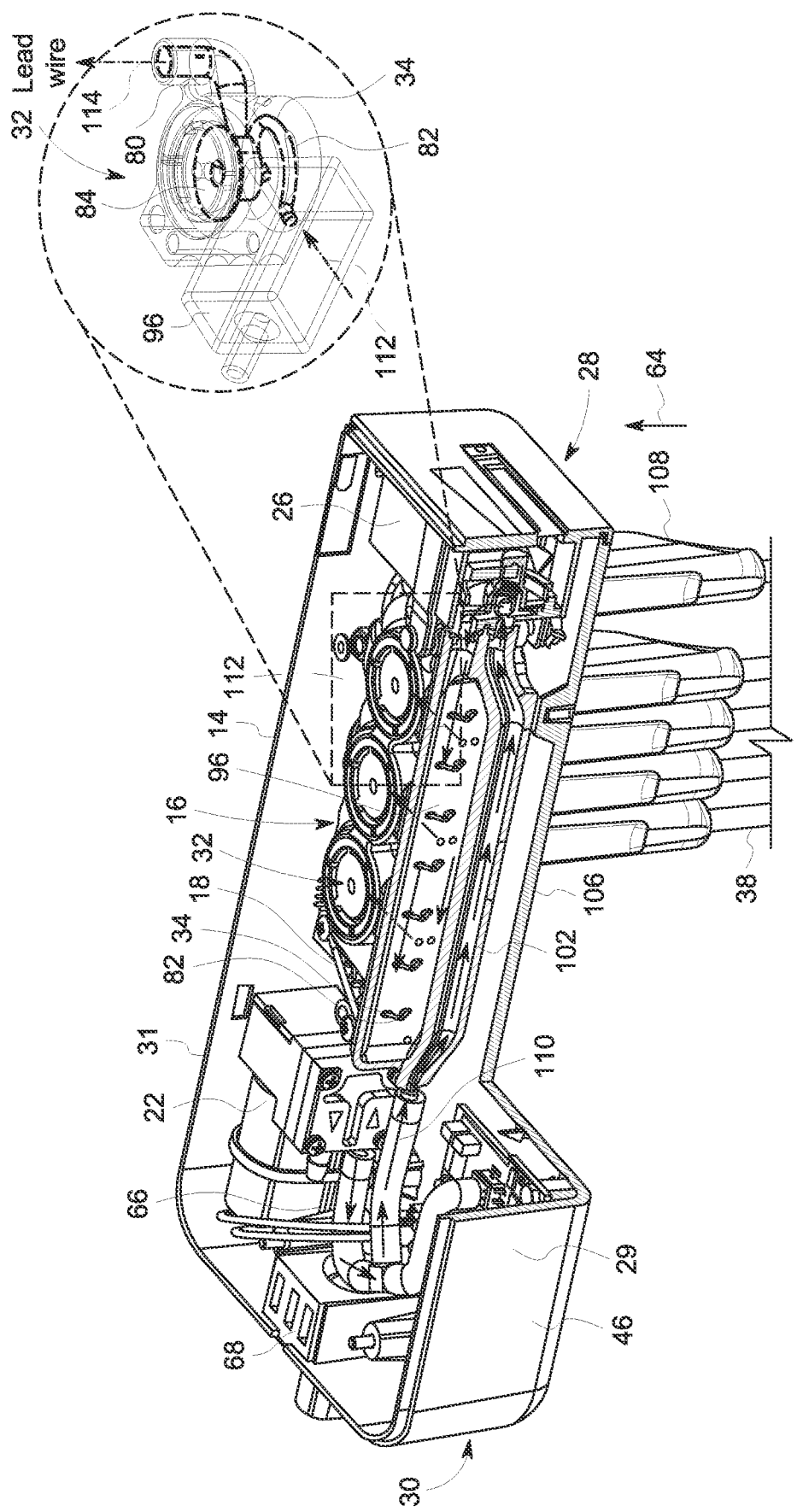
FIG. 12 is a partial cut-away view of an electrode distributor coupled to a regulator, in accordance with aspects of the present disclosure.

FIG. 12 is a partial cut-away view of the electrode distributor 12 coupled to the regulator 26. As depicted, the pump 22, the control board 24, and the suction manifold assembly 16 are disposed within the housing 14 of the electrode distributor 12. The lead wire PCB is not shown. The regulator 26 is coupled to the end 28. Tubing 66 connects the pump 22 to the manifold 18. In addition, tubing 66 connects manifold 18 to the control board 24 having the pressure sensor. The control board 24 is also connected to the pump 22. The electrode distributor 12 also includes a connection 68 for coupling to a trunk cable 70 (e.g., having a pneumatic tubing connector).

As depicted in FIG. 12, the lead wires 38 of the suction electrodes are coupled to a bottom surface 106 of the housing 14. In particular, p-connectors 108 are disposed in ports in the bottom surface 106. The p-connectors 108 extend vertically in direction 64 from the bottom surface 106. This minimizes or eliminates bending stresses in the lead wires 38, thus, improving the life span of the lead wires 38.

In the absence of triggering a vacuum via pressing a suction electrode, air flows (as indicated by arrows 110) through the tubing 66 and into the lower chamber 102 of the manifold 18. From the lower chamber 102, the air flows through the regulator 26 into the common manifold chamber 96. Air then flows from the common manifold chamber 96 into the pneumatic valves 32 via the venturi paths 34 as indicated by arrows 112. Then, the air flows through the pneumatic valves and exits the portions 80 (as indicated by arrows 114) to the lead wires 38 of the suction electrodes.

Overall due to the orifice and the venturi paths 34, in certain aspects, the mass flow rate in the system is approximately $3.036 \times 10^5$ kg/s.

Figure 13:
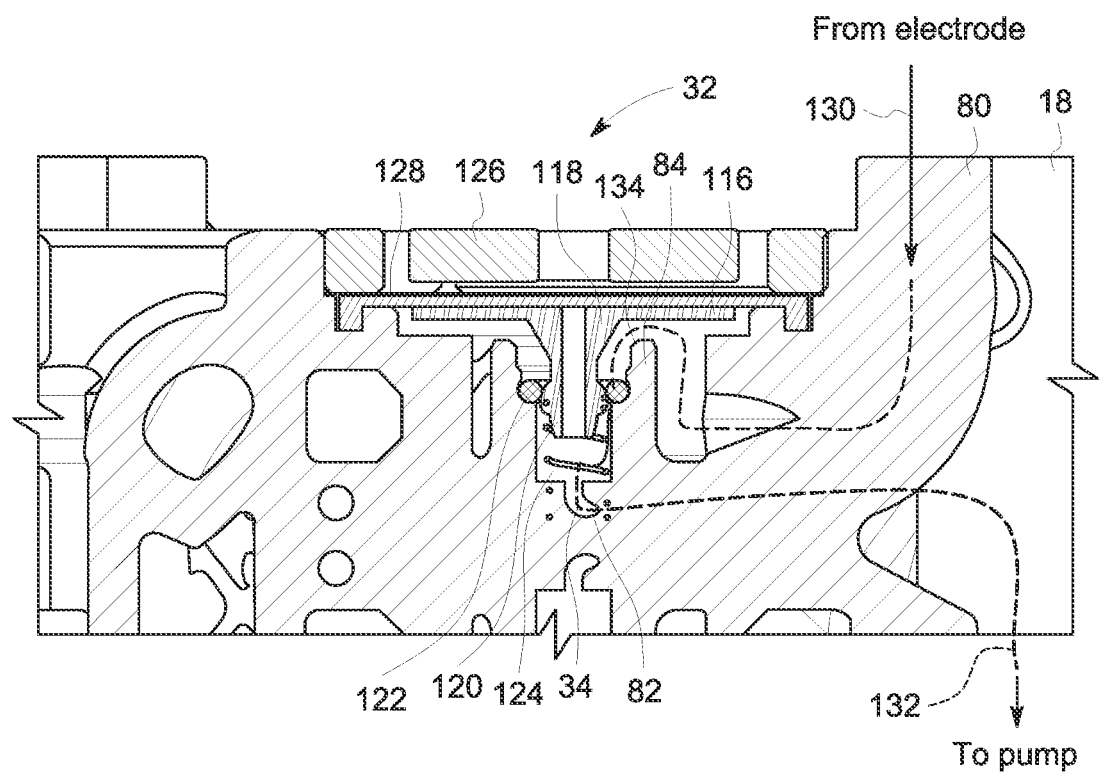
FIG. 13 is a cross-sectional view of a pneumatic valve of the ECG electrode application system in FIG. 1 (e.g., in a presence of a change in pressure from pressing a suction electrode), taken along line 13-13 of FIG. 8, in accordance with aspects of the present disclosure.
Figure 14:
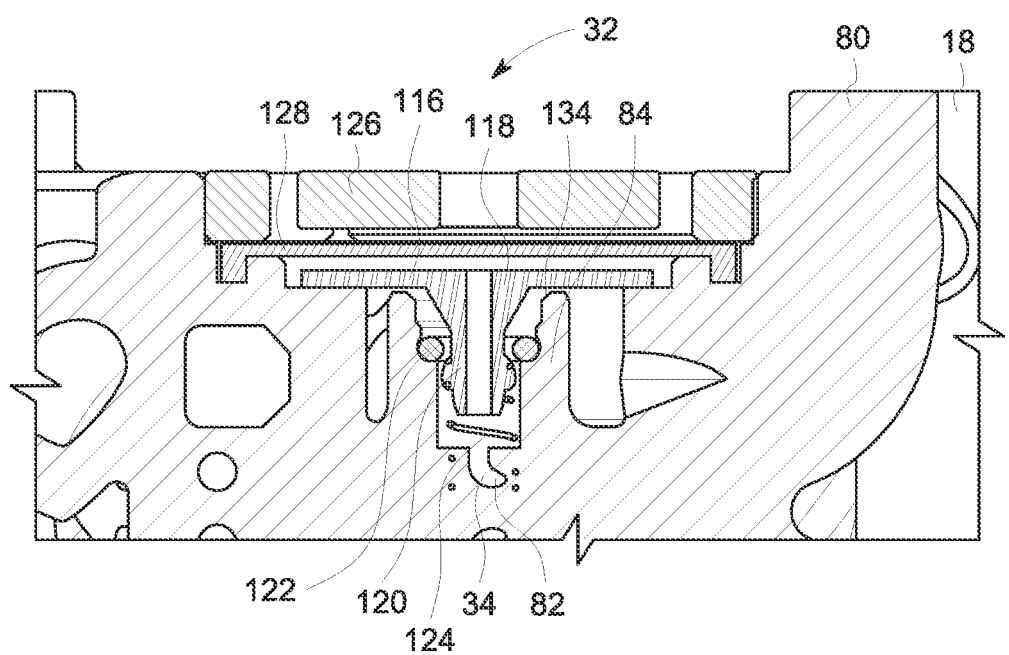
FIG. 14 is a cross-sectional view of the pneumatic valve in FIG. 14 (e.g., in the presence of a vacuum), taken along line 13-13 of FIG. 8, in accordance with aspects of the present disclosure.

FIGS. 13 and 14 are cross-sectional views of the pneumatic valve 32 taken along line 13-13 of FIG. 8. The pneumatic valve 32 includes the inlet portion 80, the outlet portion 82, and the valve body portion 84 integrated within a portion of the manifold 18 as described above. The pneumatic valve 32 also includes a plunger 116 disposed within the valve body portion. The plunger 116 includes a first end portion 118 (e.g., flat portion) and a second end portion 120. An O-ring 122 is disposed about the second end portion 120. A spring 124 is disposed about the second end portion 120 on a side of the O-ring 122 opposite the first end portion 118. A retainer ring 126 is secured to the manifold 18 to keep the plunger 116 within the pneumatic valve 32. A paper barrier 128 is disposed within the pneumatic valve 32 between the first end portion 118 and the retainer ring 126.

FIG. 13 depicts the pneumatic valve 32 in a presence of a change in pressure from pressing the suction electrode. In this state, the first end portion 118 of the plunger abuts the paper barrier 128 as pressurized air flows from the suction electrode through the portion 80 of the pneumatic valve 32 and into the valve body portion 84 as indicated by arrow 130 lifting the first end portion 118 of the plunger 116 away from a shoulder of the valve body portion 84 (i.e., actuating the pneumatic valve 32). The pressurized air then flows through the valve body portion 84 past the second end portion 120 of the plunger 116 into the venturi path 34 and to the pump (and control board having the pressure sensor) as indicated by arrow 132.

FIG. 14 depicts the pneumatic valve 32 in the presence of a vacuum (e.g., triggered by pressing the suction electrode). In the presence of the vacuum or suction pressure from the pump, the first end portion 118 of the plunger 116 abuts the shoulder 134 of the valve body portion 84 causing suction pressure on the suction electrode.

Figure 15:
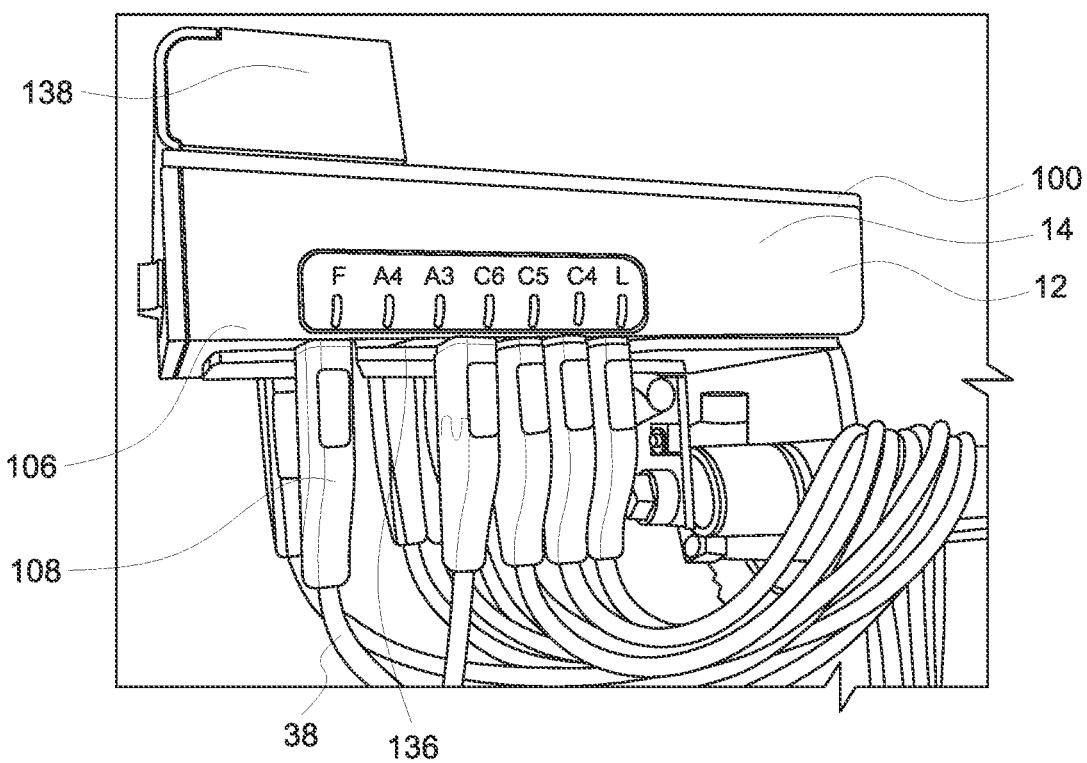
FIG. 15 is a side view of an electrode distributor of the ECG electrode application system in FIG. 1 coupled to lead wires, in accordance with aspects of the present disclosure.

FIG. 15 is a side view of the electrode distributor 12 coupled to the lead wires 38. As depicted, the lead wires 38 of the suction electrodes are coupled to the bottom surface 106 of the housing 14 of the electrode distributor 12. In particular, the p-connectors 108 are disposed in ports 136 in the bottom surface 106. The p-connectors 108 extend vertically in direction 64 from the bottom surface 106. This minimizes or eliminates bending stresses in the lead wires 38, thus, improving the life span of the lead wires 38.

In addition, the electrode distributor 12 includes a holder 138 for receiving and coupling an acquisition module (e.g., acquisition module 42 in FIG. 1) to the electrode distributor 12. The holder 138 is disposed on a top surface (e.g., the lid 100) of the electrode distributor 112.

Figure 16:
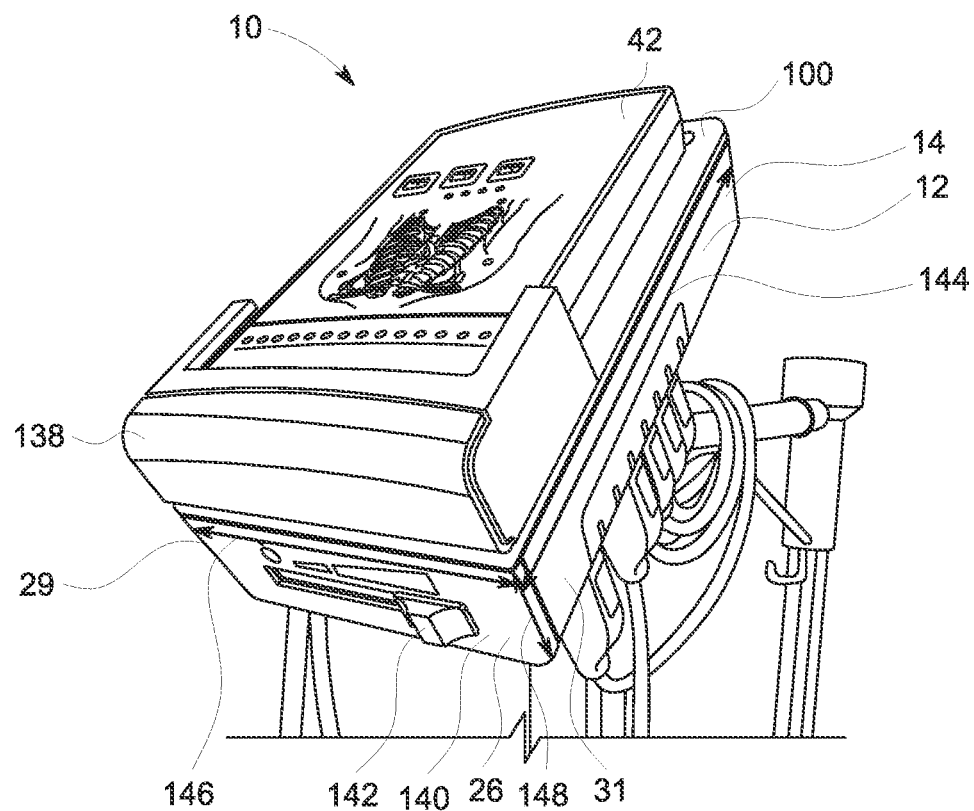
FIG. 16 is a perspective view of the ECG electrode application system in FIG. 1, in accordance with aspects of the present disclosure.

FIG. 16 is a perspective view of the ECG electrode application system 10. As depicted, the acquisition module 42 is disposed within the holder 138 on top of the electrode distributor 12. Also, depicted in FIG. 16, an outer surface 140 of the regulator 26 includes a knob 142 (e.g., slider) that may be displaced between sides 29, 31 to adjust the vacuum.

The ECG electrode application system 10 includes a more compact configuration than other ECG electrode application systems with the acquisition module 42 disposed directly over the electrode distributor 12 and the regulator 26. The electrode distributor 12 coupled to the regulator 12 includes a first dimension 144 (e.g., length), a second dimension 146 (e.g., width), and a third dimension 148 (e.g., height). Besides being more compact, the ECG electrode application system 10 is easily cleaned.

Technical effects of the disclosed aspects include providing an ECG electrode application system including an electrode distributor coupled to suction electrodes. The electrode distributor includes pneumatic valves integrated within a manifold disposed within the electrode distributor. Adjacent pneumatic valves may be arranged in both a first direction and a second direction (which are orthogonal with respect to each other) along a horizontal plane. Each pneumatic valve includes a venturi path integrated within the manifold. The venturi path determines the negative pressure (e.g., suction dome pressure) with which the suction electrode is adhered to the skin of a patient. An orifice is disposed with the common manifold chamber. The orifice determines the sensitivity (e.g., by controlling mass flow rate within the system) for pressing suction dome to trigger a pump (e.g., disposed within the electrode distributor) to cause a vacuum to create the negative pressure for adhering the suction electrodes to the skin of the patient. The utilization of the venturi paths enables a compact manifold. The combination of the venturi paths and the orifice improves triggering the use of a pump and provides sufficient vacuum transfer pressure to the suction electrodes.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112 (f). However, for any claims containing elements designated in any other manner, it is intended that such elements are not to be interpreted under 35 U.S.C. 112 (f).

This written description uses examples to disclose the present subject matter, including the best mode, and also to enable any person skilled in the art to practice the invention, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An electrocardiogram (ECG) electrode application system, comprising:
   an electrode distributor, comprising:
      a housing; and
      a suction manifold assembly disposed within the housing, wherein the suction manifold assembly comprises a manifold, a plurality of pneumatic valves integrated within the manifold, and the manifold comprises a common manifold chamber fluidly coupled to each pneumatic valve of the plurality of pneumatic valves, and each pneumatic valve comprises a venturi passage, wherein each pneumatic valve comprises a valve body portion coupled to an inlet portion, and each pneumatic valve comprises an outlet portion and a narrow portion disposed between the valve body portion and the outlet portion, and wherein the narrow portion has a diameter that is less than a respective diameter of each of the inlet portion, the valve body portion, and the outlet portion; and a plurality of suction electrodes, each suction electrode of the plurality of suction electrodes having an electrode suction dome and coupled to the electrode distributor via a lead wire, and each lead wire is coupled to a respective pneumatic valve;

wherein each electrode suction dome is configured, when pressed to cause a change in air pressure that results in a suction pressure being applied within a respective electrode suction dome, to adhere a corresponding suction electrode to a subject at a pressure determined by the venturi passage of a corresponding pneumatic valve.

2. The ECG electrode application system of claim 1, further comprising a pump disposed within the housing, wherein the pump is configured to generate a vacuum to create the suction pressure when the respective electrode suction dome is pressed.

3. The ECG electrode application system of claim 1, further comprising an orifice disposed within the common manifold chamber, wherein the orifice is configured to set a level of change in the air pressure to trigger the application of the suction pressure applied within the respective electrode suction dome.

4. The ECG electrode application system of claim 3, further comprising a regulator configured to regulate a vacuum utilized to create the suction pressure, wherein the regulator is configured to couple to the housing, and the orifice is coupled to the regulator.

5. The ECG electrode application system of claim 1, wherein the housing comprises a first surface and a second surface disposed opposite the first surface, wherein the first surface is configured to receive an acquisition module for acquiring ECG signals from the plurality of suction electrodes and the second surface is configured to receive the respective lead wires of the plurality of suction electrodes.

6. The ECG electrode application system of claim 5, wherein the first surface is a top surface and the second surface is a bottom surface.

7. The ECG electrode application system of claim 1, wherein pneumatic valves of the plurality of pneumatic valves are disposed adjacent to each other along a horizontal plane in both a first direction and a second direction, the first direction being orthogonal to the second direction.

8. The ECG electrode application system of claim 7, wherein the plurality of pneumatic valves comprises both a first set of pneumatic valves disposed along a first horizontal plane in both the first direction and the second direction and a second set of pneumatic valves disposed along a second horizontal plane in both the first direction and the second direction, the first horizontal plane being parallel with the second horizontal plane.

9. The ECG electrode application system of claim 8, wherein a number of pneumatic valves in the first set of pneumatic valves is different from a number of pneumatic valves in the second set of pneumatic valves.

10. The ECG electrode application system of claim 9, wherein the first set of pneumatic valves comprises 6 pneumatic valves and the second set of pneumatic valves comprises 8 pneumatic valves.

11. The ECG electrode application system of claim 8, wherein the first set of pneumatic valves is oriented in an opposite direction from the second set of pneumatic valves.

12. The ECG electrode application system of claim 8, wherein the first set of pneumatic valves is disposed above the second set of pneumatic valves in a vertical direction that is orthogonal to the first and second horizontal planes.

13. The ECG electrode application system of claim 1, wherein each venturi passage is integral to the manifold.

14. The ECG electrode application system of claim 13, wherein the manifold is additively manufactured.

15. A suction manifold assembly for an electrocardiogram (ECG) electrode application system, comprising:
a manifold;
a plurality of pneumatic valves integrated within the manifold;
a common manifold chamber fluidly coupled to each pneumatic valve of the plurality of pneumatic valves, and wherein each pneumatic valve is configured to be coupled via a lead wire to a respective suction electrode;
wherein the suction manifold assembly is configured to be disposed within a housing of an electrode distributor of the ECG application system, and wherein pneumatic valves of the plurality of pneumatic valves are disposed adjacent to each other along a horizontal plane in both a first direction and a second direction, the first direction being orthogonal to the second direction; and
wherein the plurality of pneumatic valves comprises both a first set of pneumatic valves disposed along a first horizontal plane in both the first direction and the second direction and a second set of pneumatic valves disposed along a second horizontal plane in both the first direction and the second direction, the first horizontal plane being parallel with the second horizontal plane, and wherein the first set of pneumatic valves is disposed in an opposite orientation from the second set of pneumatic valves.

16. The ECG electrode application system of claim 15, wherein a number of pneumatic valves in the first set of pneumatic valves is different from a number of pneumatic valves in the second set of pneumatic valves.

17. The ECG electrode application system of claim 15, wherein the first set of pneumatic valves is disposed above the second set of pneumatic valves in a vertical direction that is orthogonal to the first and second horizontal planes.

18. An electrocardiogram (ECG) electrode application system, comprising:
an electrode distributor, comprising:
a housing; and
a suction manifold assembly disposed within the housing, wherein the suction manifold assembly comprises a manifold, a plurality of pneumatic valves integrated within the manifold, and the manifold comprises a common manifold chamber fluidly coupled to each pneumatic valve of the plurality of pneumatic valves, and each pneumatic valve comprises a venturi passage, wherein each pneumatic valve comprises a valve body portion coupled to an inlet portion, and each pneumatic valve comprises an outlet portion and a narrow portion disposed between the valve body portion and the outlet portion, and wherein the narrow portion has a diameter that is less than a respective diameter of each of the inlet portion, the valve body portion, and the outlet portion;
an orifice disposed within the common manifold chamber; and
a plurality of suction electrodes, each suction electrode of the plurality of suction electrodes having an electrode suction dome and coupled to the electrode distributor via a lead wire, and each lead wire is coupled to a respective pneumatic valve;

wherein each electrode suction dome is configured, when pressed to cause a change in air pressure that results in a suction pressure being applied within a respective electrode suction dome, to adhere a corresponding suction electrode to a subject at a pressure determined by the venturi passage of a corresponding pneumatic valve, and the orifice is configured to set a level of change in the air pressure to trigger the application of the suction pressure applied within a respective electrode suction dome.

* * * * *